United States Patent [19]

Park et al.

[11] Patent Number: 5,376,692

[45] Date of Patent: Dec. 27, 1994

[54] METHOD OF BINDING USING IRRADIATION AND PRODUCT WITH ALBUMIN BOUND TO BIOMATERIALS

[75] Inventors: Kinam Park; Kalpana R. Kamath, both of West Lafayette, Ind.

[73] Assignee: Purdue Research Foundation, West Lafayette, Ind.

[21] Appl. No.: 883,651

[22] Filed: May 15, 1992

[51] Int. Cl.$^5$ .................. A61L 33/00; C08H 1/00; C08H 1/02
[52] U.S. Cl. ..................... 522/87; 523/112; 527/201; 527/204; 527/207
[58] Field of Search ............ 522/87, 111, 88, 113; 527/201, 204, 205, 206, 207; 523/112

[56] References Cited

U.S. PATENT DOCUMENTS

| | | | |
|---|---|---|---|
| 3,826,678 | 7/1974 | Hoffman et al. | 522/111 |
| 4,039,413 | 8/1977 | Kraemer | 522/87 |
| 4,722,906 | 2/1988 | Guire | 436/501 |
| 4,940,541 | 7/1990 | Aoyagi | 210/321.8 |
| 4,973,493 | 11/1990 | Guire | 427/2 |
| 4,979,959 | 12/1990 | Guire | 623/66 |
| 5,002,582 | 3/1991 | Guire et al. | 623/66 |
| 5,053,453 | 10/1991 | Ku | 523/112 |
| 5,061,750 | 10/1991 | Feijen et al. | 523/112 |
| 5,075,003 | 12/1991 | Aoyagi | 210/321.8 |
| 5,134,192 | 7/1992 | Feijen et al. | 523/112 |
| 5,165,919 | 11/1992 | Sasaki et al. | 523/112 |
| 5,167,960 | 12/1992 | Ito et al. | 523/112 |

OTHER PUBLICATIONS

C. Mathias et al., "Radiolabeling of Platelets", Seminars in Nuclear Medicine, vol. XIV, No. 2, Apr. 1984, pp. 118–127.

A. Hoffman et al., "Covalent Binding of Biomolecules to Radiation-Grafted Hydrogels on Inert Polymer Surfaces", vol. XVIII Trans. Amer. Soc. Artif. Int. Organs, 1972, pp. 10–17.

K. Part et al., "Acute surface-induced thrombosis in the canine ex vivo model: Importance of protein composition of the initial monolayer and platelet activation", Journal of Biomedical Materials Research, vol. 20, 1986, pp. 589–612.

W. G. Pitt et al., "Albumin Adsorption on alkyl derivatized polyurethanes: I. The effect of C-18 alkylation", (List continued on next page.)

*Primary Examiner*—Susan Berman
*Attorney, Agent, or Firm*—Barnes & Thornburg

[57] ABSTRACT

A medical device has one or more polymeric substrates each treated with a chemically binding coating to make each polymeric substrate compatible for contact with blood. A modified natural and substantially hydrophilic blood protein bonds permanently to each substrate. The protein is functionalized with bonding sites so after application thereof to each substrate and if subject to sufficient radiation, free radicals created on each substrate and the functionalized protein chemically bind. A modifier added to the protein creates sites by functionalizing it before application to each substrate. The functionalized combination is applied to each substrate. The protein is human or animal albumin as bovine.

The modifier are molecules having an epoxy function for attachment to the human or animal albumin. An unsaturated double bond forms or accepts free radicals at bonding sites. The modifier added to the protein is glycidyl acrylate. The bonding sites and the unsaturated double bond for attachment to free radicals are each a single carbon atom of a carbon-carbon bond which together form a covalent bond. The radiation is gamma or electron beam. The polymeric substrates in the extracorporeal circuit permit penetration of gamma rays. A method has the steps of selecting the protein; adding the modifier for creating bonding sites to functionalize the protein before application to each polymeric substrate; applying the combination to each substrate, and creating free radicals on each substrate and the combination. The method includes irradiating the combination sufficiently to create free radicals on each coated substrate as the bonding sites for chemically binding.

2 Claims, 2 Drawing Sheets

OTHER PUBLICATIONS

Journal of Biomedical Materials Research, vol. 22, pp. 359–382, 1988.

T. Grasel et al., "Effects of alkyl grafting on surface properties and blood compatibility of polyurehtane block copolymers", Journal of Biomedical Materials Research, vol. 21, pp. 815–842, 1987.

M. F. Sigot-Luizard et al., "Cytocompatibility of albuminated polyester fabrics", Journal of Biomed. Materials Research, vol. 18, pp. 895–909, 1984.

R. Sipehia et al., "Enhanced albumin binding to polypropylene beads via anhydrous ammonia gaseous plasma", Biomaterials, vol. 7, pp. 471–473, Nov. 1986.

R. C. Eberhart et al., "Influence of Endogenous Albumin Binding on Blood–Material Interactions", Annals New York Academy of Sciences, 516:78–95, 1987.

R. Siphehia, "Albuminated Polymer Surfaces for Biomedical Application", Biomat., Med. Dev., Art. Org., 10(4), pp. 229–246, 1982.

S. W. Kim et al., "Surface Modification of Polymers for improved Blood Compatibility", CRC Critical Reviews in Biocompatibility, vol. 1, Issue 3, pp. 229–260, 1985.

K. Kottke-Marchant et al., "Effect of albumin coating on the in vitro blood compatibility of Dacron ® arterial prostheses", Biomaterials, vol. 10, pp. 147–155, Apr. 1989.

J. N. Mulvihill, "Surface pasivation by human albumin of plasmapheresis circuits reduces platelet accumulation and thrombus formation. Experimental and clinical studies.", Hournal of Biomedical Materials Research, vol. 24, pp. 155–163, 1990.

D. Lyman, "Bulk and Surface Effects on Blood Compatibility", Journal of Bioactive and Compatible Polymers, vol. 6, pp. 283–295, Jul. 1991.

L. Broman, "Problems in the Development of Materials that are compatible with Blood", Med. Dev., Art. Org., 12(3–4), pp. 307–323, 1984–85.

S. Bruck, "Properties of Biomaterials in the Physiological Environment", CRC Press, Inc., Boca Raton, Fla., 23–34, 1980.

M. H. Rao et al., "Radiation Induced Grafting of Mixed Monomers onto Polyester and Polypropylene Fibers", Journal of Applied Polymer Science, vol. 33, pp. 2707–2713, 1987.

J. Woolston, "Irradiation Sterilization of Medical Devices", Medical Device Technology, pp. 1–8, Jul./Aug. 1990.

A. Hoffman, "Ionizing Radiation and Gas Plasma (or Glow) Discharge Treatments for Preparation of Novel Polymeric Biomaterials", Ctr. for Bioengineering and Dept. of Chem. Enginnering, University of Washington, Seattle, Wash., pp. 141–157, 1983.

S. Lin et al., "Heparin immobilization increased through chemical amplification", Journal of Biomedical Materials Research, vol. 25, pp. 791–795, 1991.

E. Wilkins et al., "Biomaterials for Implanted Closed Loop Insulin Delivery System: A Review", Biosensors and Bioelectronics, pp. 167–213, 1990.

T. Chandy et al., "Biocompatiblity and Toxicological Screening of Materials", Sree Chitra Tirunal Institute for Med. Sciences and Technology, Poojapura, India, pp. 131–140, date unknown.

V. A. Postnikov et al., "The Simple Preparative Synthesis of Graft Copolymers of Polyethylene–Acrylamide", Polymer Bulletin 3, pp. 75–81, 1980.

V. Kalliyana Krishnan et al., "Radiation grafting of hydrophilic monomers on to plasticized poly(vinyl chloride) sheets", Journal of Materials Science: Materials in Medicine 1 pp. 185–191, 1990.

C. Sharma, "Surface Modification: Blood Compatibility of Small Diameter Vascular Graft", Sree Chitra Tirunal Inst. f. Med. Sciences and Technology, Poojapura, India, pp. 25–31, date unknown.

H. Nossel et al., "Importances of Polar Groups for initiating Blood Coagulation and aggregating Platelets", Nature, vol. 221, pp. 75–76, 1969.

N. Plate, "Trypsin Macromonomer and its copolymerization with Hydrophilic Monomers", Vysokomol. soyed. A31: No. 1, pp. 195–197, 1989.

P. Edman, "Immobilization of Proteins in Microspheres of Biodegradable Polyacryldextran", Journal of Pharmaceutical Sciences, vol. 69, No. 7, pp. 838–842, Jul. 1980.

K. Bergstrom et al., "Protein Immobilization to Polystyrene via Long Poly(ethylene Glycol) Chains", Biotechnology and Bioengineering, vol. 38, pp. 952–955, 1991.

D. Leckband et al., "An Approach for the Stable Immobilization of Proteins", Biotechnology and Bioengineering, vol. 37, pp. 227–237, 1991.

S. Snyder et al., "An Improved 2,4,6–Trinitrobenzenesulfonic Acid Method for the Determination of Amines", Analytical Biochemistry 64, pp. 284–288, 1975.

J. D. Andrade, "Water as a Biomaterial", vol. XIX Trans. Amer. Soc. Artif, Int. Organs, pp. 1–7, 1973.

D. F. Williams, "Biomaterials and Biocompatibility: An Introduction", Fundamental Aspects of Biocompatibility, pp. 1–7, date unknown.

C. Forbes et al., "Thrombus Formation and Artificial Surfaces", British Med. Bulletin, vol. 34, No. 2, pp. 201–207, 1978.

A. Hoffman, "Future Trends in Biomaterials Research and Development", Artificial Organs, vol. 15, No. 4, Abstract No. 118, 1991.

D. Kiaei, "Albumin Retention by Glow Discharge Deposited Polymers", Artifical Organs, vol. 15, No. 4, Abstract No. 121, 1991.

N. A. Plate, et al., "Structure of the Heparin Macromonomer and Features of its Radical Polymerization", Vysokomol. soyed. A31: No. 1, pp. 220–227, 1989.

J. Singh, et al., "Studies on Grafting of Methoacrylic Acid on to Poly(vinyl chloride) Films", British Polymer, Journal 22, pp. 89–95, 1990.

P. N. Sawyer, M.D., et al., "Electrode–Biologic Tissue (List continued on next page.)

OTHER PUBLICATIONS

Interractions at Interfaces–A Review", Biomat., Med. Dev., Art. Org. 12(3–4), pp. 161–196, 1984–85.

L. Vroman et al., "Reactions of Formed Elements of Blood with Plasma Proteins at Interfaces", Annals New York Academy of Sciences, pp. 65–76, date unknown.

N. A. Plate et al., "Acylation of Serum Albumin by Unsaturated Chlorides", Polymer Science, USSR, vol. 24, No. 11, pp. 2668–2671, 1982.

R. Eberhart et al., "Protein Adsorption on Polymers", American Chemical Society, pp. 293–315, 1982.

"Bioincompatbility: an overview", The Int'l Journal of Artifical Organs, vol. 12, No. 6, pp. 356–365. 1989.

N. Larsson et al., "New biomaterial for better health care equipment", Technology Magazine, No. 2, pp. 49–59, Aug. 1990.

V. D. McGinniss, "Cross–Linking with Radiation", Batelle Columbus Laboratories, vol. 4, pp. 418–449, date unknown.

Purdue University, "Thermografting of Albumin onto Polypropylene Films", The Association of the advancement of Medical Instrumentation, pp. 1–3, Dec. 1991.

T. Matsuda et al., "Novel Photoreactive Surface Modification Technology for Fabricated Devices", vol. XXXVI, Trans Am Soc Art Intern Organs, pp. 161–164, 1990.

S. Q. Liu et al., "Synthesis and non–thrombogenicity of polyurethanes with poly(oxyethylene) side chains in soft segment regions", J. Biomater, Sci. Polymer Edn, vol. 1, No. 2, pp. 111–122, 1989.

C. Sharma et al., "Radiation–Induxed Albuminated Surfaces–Their Modifications toward Blood Compatibility", Hournal of Colloid and Interface Science, vol. 97, No. 1, pp. 38–40, 1984.

C. Tsai et al., "Biocompatible Coatings with High Albumin Affinity", Dept. of Surgery and Biomedical Engineering Program, University of Texas Southwestern Med. Ctr. at Dallas, and the University of Texas at Arlington, pp. 307–310, date unknown.

METHOD OF BINDING USING IRRADIATION AND PRODUCT WITH ALBUMIN BOUND TO BIOMATERIALS

FIELD OF THE INVENTION

This relates to functionalizing proteins for binding to polymers in an extracorporeal circuit with radiation, and more specifically covalently binding bovine albumin modified with glycidyl acrylate to polymers by gamma irradiation.

BACKGROUND OF THE INVENTION

Research on the thrombus formation on artificial biomaterials has produced information on protein adsorption and platelet activation on the surface. Despite such endeavor, the surface-induced platelet activation still remains a major hurdle in the successful long-term implantation of biomaterials. Although numerous approaches have been made to improve the blood compatibility of biomaterials, few approaches are practical enough to be used. Thus, it is necessary to develop a simple procedure for the modification of biomaterial surfaces without causing adverse effects on the functional properties of both the substrate polymer surface and the grafted moiety.

Biomaterials and Biocompatibility

There has been an increasing interest in improving the biocompatibility of various biomaterials such as heart valves, pacemakers, vascular implants, sutures, orthopedic devices, and contact lenses (Larsson, N., Lenz, G., and Okuzumi, Y., *New biomaterials for better health care equipment*, Technology Magazine, 12: 49–59, 1990). The concept of biocompatibility involves the chemical interactions that take place between the body and the material as well as the physiological responses to these reactions. Hence, a biocompatible material is the one which is able to exist within a body without adversely affecting the body and causing undesired effects (Williams, D. F., *Biomaterials and Biocompatibility. in Fundamental Aspects of Biocompatibility*, D. F. Williams, ed., Florida, CRC Press, 1, 1–10, 1981).

Blood compatibility may be defined as the inability of the surface to activate the intrinsic coagulation system or to attract or alter platelets or leukocytes (Forbes, C. D. and Prentice C. R. M., *Thrombus formation and artificial surfaces*, Brit. Med. Bull. 34, 201–207, 1978). The first event that occurs when a foreign object is placed in contact with blood is the deposition of a protein layer on the intruding surface. This is followed by adhesion and aggregation of platelets, eventually leading to formation of thrombi on the material surface (Forbes, C. D. and Prentice C. R. M., *Thrombus formation and artificial surfaces*, Brit. Med. Bull. 34, 201–207, 1978; Vroman, L., Adams, A. L., Klings, M., Fischer, G. C., Munoz, P. C., and Solensky, R., *Reactions of formed elements of blood with plasma proteins at interface*. Ann. N.Y., Acad. Sci., 283, 65–76, 1977). The fact that surface properties are related to blood compatibility has been recognized for a while. Research in past suggests that prosthesis-blood interaction, initiated by the initial protein adsorption, is influenced by a combination of factors, including surface charge (Sawyer, P. N., *Electrode-Biologic tissue interactions at interface-A Review*, Biomat. Med. Dev. Art. Org. 12, 161–196, 1984–85; Bruck, S. D., *Properties of Biomaterials in the Physiological Environment*, CRC Press, Inc., Boca Raton, Fla., pp 23, 1980; Nossell, H. L., Wilneer, G. D., and LeRoy, E. C., *Importance of polar groups for initiating blood coagulation and aggregating platelets*, Nature (Lond.), 221, 75, 1969), surface free energy and wettability (Sharma, C. P., *Surface modification: Blood compatibility of small diameter vascular graft*. in Blood Compatible Materials and Devices, Sharma, C. P. and Szycher, M., Eds., Technomic Publishing Co. Int., pp 25–31, 1991; Andrade, J. D., Lee, H. B., John, M. S., Kim, S. W., and Hibbs, J. B. Jr., *Water as a biomaterial*, Trans. Amer. Soc. Artif. Int. Org., 19, 1, 1973), surface roughness and porosity (Wilkins, E., and Radford. W., *Biomaterials for implanted closed look insulin delivery system: A Review. Biosensors and Bioelectronics*, 5, 167–213, 1990), chemical structure (Lyman, D. J., *Bulk and Surface Effects on blood compatibility*, J. Bioactive and Biocompatible Polymers, 6, 283–295, 1991), and flow conditions (Vroman, L., *Problems in the development of materials that are compatible with blood*, Biomat. Med. Dev. Art. Int. Org., 12, 307–323, 1984–85).

Despite these advances, no biomaterial has been able to match the endothelial surface in terms of its thromboresistant properties (Vanholder, R. and Ringoir, S., *Bioincompatibility: An overview*, Int. J. Artif. Organs., 5, 297–303, 1982; Chandy, T. and Sharma, C. P., *Biocompatibility and Toxicological Screening of Materials*. in Blood Compatible Materials and Devices, Sharma, C. P. and Szycher, M., Eds., Technomic Publishing Co., Int., pp 131–140, 1991). Surface-induced platelet activation still remains one of the major problems in the successful long-term implantation of biomaterials. Although numerous approaches have been tried to improve the blood compatibility of biomaterials, few are practical enough to be used for producing clinical biomaterials. The next section describes approaches that have been used to modify the biomaterial surfaces and improve biocompatibility.

A number of investigations on platelet-surface interactions have indicated that the presence of albumin on the surface decreases the surface-induced platelet activation (Kim, S. W. and Feijen, J.: *CRC Crit. Rev. Biocompatibility*, 1: 229–260, 1985; Kotte-Marchant, K., Anderson, J. M., Umemura, Y. and Marchant, R. E.: *Biomaterials*, 10: 147–155, 1989; Mulvihill, J. N., Faradji, A., Oberling, F. and Cazenave, J-P.: *J. Biomed. Mater. Res.*, 24: 155–163, 1990; Park, K., Mosher, D. F., and Cooper, S. L.: *J. Biomed. Mater. Res.*, 20: 589–612, 1986).

The total number of adherent platelets and the extent of platelet activation are reduced on the albumin-coated surfaces. For this reason, several approaches for albumin immobilization have been considered. Albumin can be physically adsorbed on biomaterial surfaces prior to implantation (Mulvihill, J. N., Faradji, A., Oberling, F. and Cazenave, J-P.: *J. Biomed. Mater. Res.*, 24: 155–163, 1990; Park, K., Mosher, D. F., and Cooper, S. L.: *J. Biomed. Mater. Res.*, 20: 589–612, 1986). The affinity of albumin to the surface can be substantially enhanced by modifying the surface with C18 alkyl chains (Eberhart, R. C., Lynch, M. E., Bilge, F. H., Wissinger, J. F., Munro, M. S., Ellsworth, S. R., and Quattrone, A. J.: *Adv, Chem. Ser.* 199:293–315, 1982; Munro, M. S., Eberhart, R. C., Maki, N.J., Brink, B. E. and Fry, W. J.: *ASAIOJ.* 6: 65–75, 1983; Pitt, W. G. and Cooper, S. L.: *J. Biomed, Mater. Res.*: 22: 359–382, 1988; Grasel, T. G., Pierce, J. A., and Cooper, S. L.: *J. Biomed. Mater. Res.*, 21: 815–842, 1987) or with glow discharge, (Kiaei, D., Horbett, T. A., and Hoffman, A.: *Artificial Organs.* 15, 302, 1991).

Although the retention of albumin can be increased by surface modifications, physically adsorbed albumin molecules are easily displaced by other thrombogenic proteins such as fibrinogen in the blood. Thus, simple adsorption of albumin is inadequate to create blood-compatible surfaces for long-term applications. It is preferred to anchor albumin molecules to the surface through covalent bonding. Covalent bonding of albumin to different polymer surfaces has been attempted by chemical immobilization (Hoffman, A. S., Schmer, G., Harris, C., and Kraft, W. G.: *Trans, Amer, Soc. Artif. Int. Organs*, 18, 10–17, 1972). Chemical immobilization requires chemically active groups such as amine, hydroxyl or carboxyl groups on the material surface. Those groups can be introduced to the surface by plasma surface modification (Sipehia, R., Chawla, A. S., and Chang, T. M. S.: *Biomaterials*, 7, 471–473, 1986; Sipehia, R. and Chawla, A. S.: *Biomat, Med. Dev, Art. Org.* 10, 229–246, 1982).

In the absence of the functional groups on the surface, albumin molecules react with each other rather than reacting with the surface (Sigot-Luizard, M. F., Domurado, D., Sigot, M., Guidon, R., Gosselin, C., Marios, M., Girard, J. F., King, M., and Badour, B.: *J. Biomed. Mater. Res.*, 18: 895–909, 1984). Photoactivatable crosslinking agents may not require the functional groups on the biomaterial surface (Matsuda, T. and Inoue, K.: *Trans. Am. Soc. Artif. Inter. Organs.* 36: 161–164, 1990; Guire, P. E.: U.S. Pat. No. 4,979,959, 1990; Work, T. S., and Burdon, R. H.: *Photogenerated Reagents in Biochemistry and Molecular Biology*, Elsevier, Amsterdam, 1983). The surface has to be exposed to ultraviolet light and this makes the photografting on devices of complex shape or on fully assembled devices impractical. A recent study showed that albumin molecules modified with photoactivatable agents can be grafted to polymers by temperature increase (Park, K., and Tseng, Y-C.: *Proceedings of Cardiovascular Science and Technology Conference*, 1991, p 143). The temperature has to be increased to 100° C. and this would limit applications in connection with temperature sensitive materials.

Biomaterial surfaces have been modified by physical adsorption or covalent grafting of biocompatible agents. The physical adsorption of biocompatible agents is not desirable since the adsorbed agents are usually removed from the surface quite rapidly upon exposure of the surface to physiological fluid such as blood.

The covalent grafting of biocompatible agents usually involves chemical reactions between functional groups introduced to both the surface and the grafting agents. Covalent binding by chemical immobilization has been used to attach various moieties such as heparin (Lin, C. S., Jacobs, H. A., and Kim, S. W., *Heparin immobilization increased through chemical amplification*, J. Biomed. Mater. Res., 25, 791–795, 1991), or polyethylene glycol (Liu, S.Q., Ito, Y., and Imanishi, Y.: *Synthesis and non-thrombogenicity of polyurethanes with poly-(oxyethylene) side chains in soft segment regions*, J. Biomater. Sci. Polymer Edn., 1: 111–122, 1989). This method requires the presence of chemically active groups such as amine, hydroxyl or carboxyl groups on the biomaterial surface. Many biomaterials are chemically inert, i.e., no chemically active functional groups exist on the surface. In addition, grafting by chemical reactions requires involvement of a number of steps making the process time consuming and expensive. Furthermore, chemical reagents used during the grafting process may be difficult to remove at the end of grafting. Thus, it is desirable to use grafting agents which do not require functional groups on the surface.

Grafting in the absence of the chemically functional groups on the surface can be done using photoactivatable agents. Photoactivation by ultraviolet light activates a photosensitive moiety attached to the grafting agent. Although the use of photoactivatable grafting agents by ultraviolet irradiation (17; P. E. Guire, U.S. Pat. No. 4,979,959) has been successful, it has a serious limitation due to low energy nature of the UV light. The UV light cannot penetrate through polymers and thus the surface to be grafted has to be exposed to the light. This approach is not practical for the devices which are complex in shape, long in length and for the fully assembled devices, since the UV light will not be able to reach the inner parts of such devices.

Photochemical activation of reactive groups attached to albumin requires direct exposure of the albumin and the surface to ultraviolet (UV) light at the same time. Upon UV irradiation, photoreactive groups will generate nitrenes or carbenes (that have life times of milliseconds) which result in covalent bonds with almost anything including water molecules. Thus, the grafting to the surface is possible only by forming nitrenes or carbenes that are in intimate contact with the surface.

UV light cannot penetrate polymers. Thus, if the surface is not exposed to UV light, grafting will not occur. Preexposure of the surface to UV light in the absence of photoreactive albumin will do nothing. Since it is nitrenes or carbenes formed from photoreactive groups that is responsible for grafting, preexposure of the surface alone will not result in any grafting. Preexposure of the photoreactive albumin in the absence of the surface will not result in grafting, since the life times of the formed nitrenes or carbenes are milliseconds. As described, the photografting and the γ-grafting are totally different than each other. The term "photochemically" is not the same as the gamma radiation activated.

Thus, it is necessary to use high energy radiations such as electron beam irradiation or cobalt-60 gamma radiation which have a greater penetration ability. These high energy rays are different from the ultraviolet light in terms of the wavelength range, energy and hence penetration ability (McGinnis, V. D., *Cross-linking with radiation*, vol. 4, pp 418–449; Hoffman, A. S., *Ionizing radiation and gas plasma (or glow) discharge treatments for preparation of novel polymeric biomaterials*, pp 141–157). The electron beams penetrate up to approximately 4 cm, while gamma irradiation has a penetration capability of about 5 times greater than the electron beam radiation (Woolston, J., *Irradiation sterilization of medical devices*, Medical Device Technology, July–August, 1990).

Gamma irradiation has been used to graft water-soluble synthetic polymers on biomaterials by polymerizing hydrophilic monomers (Kalliyana Krishnan, V., Jayakrishnan, A., and Francis, J. D., *Radiation grafting of hydrophilic monomers onto plasticized poly(vinyl chloride) sheets*, J. Mater. Sci: Materials in Medicine, 1, 185–191, 1990; Rao, M. H., Rao, K. N., Lokhande, H. T., and Teli, M. D., *Radiation induced grafting of mixed monomers onto polyester and polypropylene fibers*, J. Appl. Poly. Sci., 33, 2707–2714, 1987; Postnikov, V. A., Lukin, N. J., Maslov, B. V. and Plate, N. A., *The simple*

*preparative synthesis of graft copolymers of polyethyleneacrylamide*, Polymer Bulletin, 3, 75–81, 1980; Singh, J., Ray, A. R., and Singh, H., *Studies on grafting of methacrylic acid onto poly(vinyl chloride) films*, Brit. Poly. Journal., 22, 89–95, 1990).

A major problem involved in using monomers to achieve graft polymerization is removal of the residual monomer and solvent at the end of the process. Since most of the monomers used for this purpose (e.g., methacrylic acid, acrylamide, acrylic acid, N-vinyl pyrrolidone, 2-hydroxyethylmethacrylate, etc.) are toxic in nature, removal of the unreacted monomer is necessary, especially when used for the modification of a biomaterial. When devices of complex shapes are treated in this manner, the problem is worse, since complete removal of the toxic, unreacted species can not be ensured. The homopolymers formed during gamma irradiation which are not grafted but are present in the bulk solution also need to be removed though they may not pose as severe a problem as that of their respective monomer counterparts.

Introduction of double bonds to biomolecules such as albumin, (Plate, N. A., Postnikov, in. A., Lukin, N. Y., Eismont, M. Y. and Grudkova, G.: *Polymer Sci. U. S. S. R.*, 24, 2668–2671, 1982) heparin, (Plate, N. A., Malykh, A. V., Uzhinova, A. D., Panov, V. P., and Rozenfeld, M. A.: *Polymer Sci, U.S. S. R.*, 31, 220–226, 1989) dextran, (Edman, P., Ekman, B., and Sjoholm, I.: *J. Pharm. Sci.*, 69, 838–842, 1980) and trypsin (Plate, N. A., Malykh, A. V., Uzhinova, A. D. and Mozhayev, V. V.: *Polymer Sci. U.S. S. R.*, 31, 216–219, 1989) has been reported in the past. Those functionalized moieties have not been used for grafting to biomaterials for the improvement of biocompatibility.

There has been a report on the grafting of albumin on the polyetherurethane surfaces by γ-irradiation (Sharma, C. P. and Kurian, G.: *J. Colloid Interf. Sci.*, 97: 38–40, 1984). The adsorbed albumin was dried in a vacuum oven before γ-irradiation. According to these studies the procedure was not effective in preventing platelet adhesion. This could be attributed to the failure in albumin grafting for two reasons. First, the albumin molecules were not functionalized, i.e., no double bonds were introduced to albumin molecules. Thus, no free radicals were formed with γ-irradiation. Second, γ-irradiation in the dried state did not result in grafting even if albumin molecules were functionalized. The approach described herein assures covalent grafting of albumin to any polymer surfaces.

U.S. Pat. Nos. 4,940,541 and 5,075,003 approach grafting a hydrophilic compound by gamma irradiation. Hydrophilic porous hollow fiber membranes, such as cuprammonium regenerated cellulose membranes, are readily swollen in the presence of water or other aqueous solutions. The swelling results in occlusion or contraction of the pores in the porous hollow fiber membranes and thus blood cannot be cleaned. To avoid such problems, it is preferred to use hydrophobic porous hollow fiber membranes on which hydrophilic compounds are grafted. The hydrophilic compounds are small molecular-weight compounds such as glycerol. They are grafted at the inner surface of the hydrophobic porous hollow fiber through the agency of a gamma ray. The modified hydrophobic hollow fiber membranes are used to remove blood-protecting liquid components such as glycerol which is contained in the preserved blood. In one example, 8 Mrad of gamma ray was used to graft glycerol after the hollow fibers were filled with glycerol. There is no evidence that glycerol is covalently grafted.

Attempts were made to graft albumin without double bonds to the surface by gamma irradiation (Sharma and Kurian; J. *Colloid Interf. Sci.*, 97: 38, 1984) which did not work. The approach described in the patents '541 and '003 cannot be used to improve the blood compatibility of the hydrophobic hollow fiber membranes, because the glycerol on the surface, even if it is grafted, cannot prevent platelet activation because its size is not large enough to repel platelets with glycerol grafted by exposing the porous hollow fiber to gamma ray. Gamma irradiation used at a dosage in the range of 0.1 to 25 Mrad, preferably 2.5 to 10 Mrad., and in the example provided, 8 Mrad. Many polymers including polypropylene which is claimed to be the best material for porous hollow fibers cannot be irradiated at more than 1 Mrad. Above that dosage, polypropylene will disintegrate over time.

Clearly, it is necessary to develop a procedure which can be used to modify chemically inert polymer surfaces irrespective of the presence or absence of functional groups by a minimum number of steps which do not cause adverse effects on the functional properties of either the substrate polymer surface or the grafted moiety. A method of improving blood compatibility of various polymeric biomaterials by covalent grafting of albumin to the surface is needed.

SUMMARY OF THE INVENTION

A medical device or a complete extracorporeal blood handling circuit may have one or more polymeric substrates each treated with a chemically binding coating to make each polymeric substrate compatible for contact with blood. A modified natural and substantially hydrophilic blood protein permanently bound to each polymeric substrate forms biologically compatible blood contacting surfaces resistant to the formation of thrombin, deposition of formal blood elements, or foreign body reaction. The modified natural and substantially hydrophilic blood protein is functionalized with bonding sites so after application thereof to each polymeric substrate it is subjected to radiation sufficient to create free radicals on each polymeric substrate for chemically binding with the bonding sites.

The modifier added to the natural and substantially hydrophilic blood protein creates bonding sites by functionalizing the natural and substantially hydrophilic blood protein before application to each polymeric substrate. The functionalized combination of the natural and substantially hydrophilic blood protein and the modifier is applied to each polymeric substrate. Free radicals are preferably formed on each polymeric substrate and the applied functionalized combination of the natural and substantially hydrophilic blood protein by treatment of the combination with radiation sufficient to create the free radicals for chemically binding at the binding sites.

The natural and substantially hydrophilic blood protein for permanent bonding to each polymeric substrate may include human or animal albumin. The modifier added to the natural and substantially hydrophilic blood protein for creating bonding sites by functionalizing the albumin for application to each polymeric substrate may include molecules having an epoxy function for attachment to the albumin. A means for attachment between the albumin and an unsaturated double bond thereby either forms or accepts free radicals on each polymeric substrate. Bonding sites may have unsaturated double bonds which form or receive the free radicals on each polymeric substrate. The modifier added to the natural and substantially hydrophilic blood protein for creating bonding sites by functionalizing the natural and substantially hydrophilic blood protein before application to the polymeric substrate preferably includes molecules having an epoxy function for attachment between the human or animal albumin and unsaturated double bonds which attach to the free radicals on the polymeric substrate.

The natural and substantially hydrophilic blood protein for permanent bonding to each polymeric substrate for forming biologically compatible blood contacting surfaces resistant to the formation of thrombin, deposition of formal blood elements or foreign body reaction is most preferably bovine albumin, but can be human albumin, too. The modifier added to the natural and substantially hydrophilic blood protein for creating bonding sites by functionalizing the animal albumin for application to each polymeric substrate may include glycidyl acrylate having the epoxy function for attachment between the animal albumin and the unsaturated double bond for forming and receiving free radicals on each polymeric substrate.

The bonding sites and the unsaturated double bond for attachment to free radicals on each polymeric substrate are preferably each a single carbon atom of a carbon-carbon bond which together form a covalent bond. The radiation may be selected from the group consisting of gamma or electron beam. The radiation may include gamma rays. The polymeric substrates in the extracorporeal circuit permit the passage of the gamma rays so that modified inside surfaces (polymeric substrates) can be treated by gamma radiation.

A method of chemically binding a coating to a medical device or an extracorporeal blood handling circuit having one or more polymeric substrates to make each polymeric substrate compatible for contact with blood preferably has steps including:

selecting the natural and substantially hydrophilic blood protein for permanent bonding to each polymeric substrate for forming biologically compatible blood contacting surfaces resistant to the formation of thrombin, deposition of formal blood elements or foreign body reaction;

adding the modifier to the natural and substantially hydrophilic blood protein for creating bonding sites by functionalizing the natural and substantially hydrophilic blood protein before application to each polymeric substrate;

applying the functionalized combination of the natural and substantially hydrophilic blood protein and the modifier to each polymeric substrate, and creating free radicals on each polymeric substrate between the applied functionalized combination of the natural and substantially hydrophilic blood protein.

The method may further have the step of creating free radicals by irradiating the combination with radiation sufficient to create free radicals on each coated polymeric substrate for the bonding sites so they may chemically bind. The method may also include the step of adding a modifier to the natural and substantially hydrophilic blood protein for creating bonding sites to functionalize the natural and substantially hydrophilic blood by preferably attaching the epoxy function to the natural and substantially hydrophilic blood protein thereby providing the unsaturated double bond for attachment to free radicals on each polymeric substrate.

The method improves blood compatibility of various polymeric biomaterials by covalent grafting of albumin to the surface. Double bonds introduced to albumin molecules by reacting with glycidyl acrylate or related chemical reagents to functionalize albumin molecules so they may be adsorbed to biomaterials and covalently grafted to the surface by means of γ-irradiation. Upon γ-irradiation, the double bonds on albumin molecules and polymer chains of biomaterials generate free radicals which react with each other to form covalent bonds. Because gamma radiation can penetrate the polymer substrates, the process is substantially easier and simpler than albumin grafting techniques on separate pieces. Thus, the preferred method can be applied to the grafting of albumin on the fully assembled products by virtue of high energy rays. Since free radicals can be generated on any polymer surface this process can be applied even to chemically inert polymers such as polyethylene or polypropylene.

DETAILED DESCRIPTION OF THE INVENTION

Preparation of Functionalized Albumin

Figure 1:
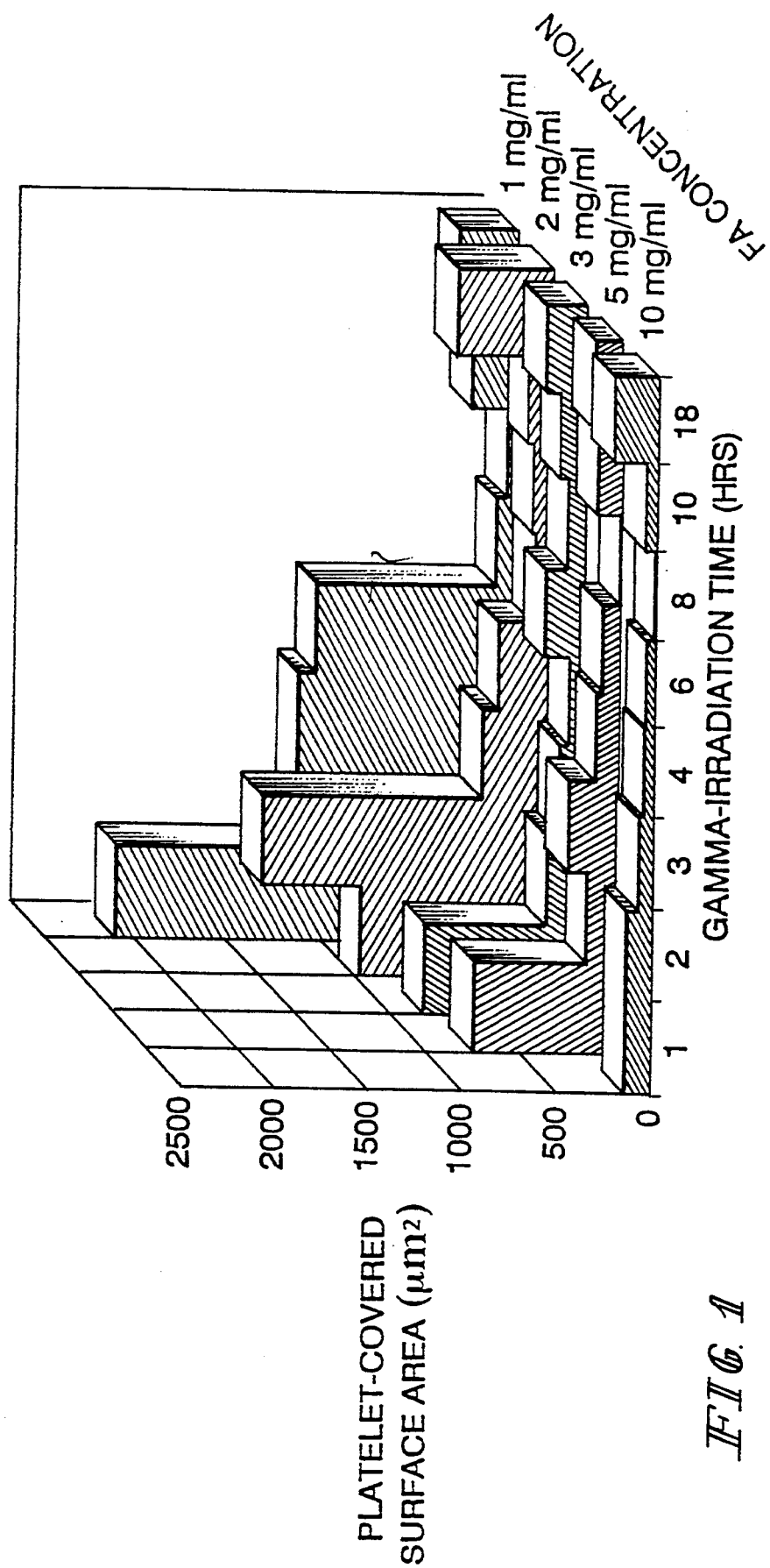
FIG. 1 is a plot of the data on the result of thrombus formation on polypropylene fibers having albumin grafted under various conditions.

Functionalized albumin molecules (albumin molecules with double bonds) were prepared by the following procedure. Human or bovine serum albumin was dissolved in phosphate-buffered saline solution diluted by a factor of 2 ($\frac{1}{2}$×PBS, pH 7.2). The final albumin concentration was 50 mg/ml. Glycidyl acrylate from Aldrich was added directly to the albumin solution while stirring. Many other reagents can be used to introduce double bonds to albumin molecules. For example, 3,4-epoxy-1-butene, 1,2-epoxy-5-hexene, glycidyl methacrylate, 1,2-epoxy-7-octene, allyl glycidyl ether, acrolein, methacrolein, acryloyl chloride, or methacryloyl chloride can be used.

Preferably, 0.8 ml of glycidyl acrylate was added to 20 ml of albumin solution. The functionalization reaction was allowed to proceed during constant magnetic stirring at room temperature. After 49 hours, 4 ml of 20 (w/v) % glycine solution was added and stirring continued for another 30 minutes. This solution was then dialyzed against $\frac{1}{2}$×PBS for two days with ten changes of the buffer solution.

The degree of albumin functionalization was determined by measuring the free amine groups of albumin using 2,4,6-trinitrobenzenesulphonic acid as per (Snyder, S. L., and Sobocinski, P. Z.: *Anal. Biochem.*, 64: 284, 1975). In the experimental condition discussed herein, the albumin functionalization was found to be 90% of the total amine groups available for the titration. The concentration of functionalized albumin for grafting was varied by diluting the concentrated functionalized albumin solution. The albumin concentration was determined spectrophotometrically. Absorptivities used for 0.1% bovine and human serum albumin solution at 280 nm were 0.64 and 0.58, respectively.

The chemical reaction involved in the above functionalization procedure is as follows:

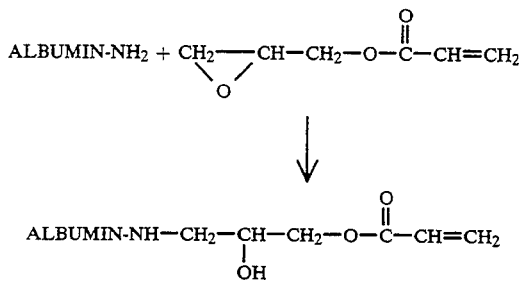

The isoelectric point of the native and functionalized bovine serum albumin were determined using Ampholine gels. Functionalized albumin showed a pI of 4.07 lower than 4.91 of the native albumin. This may be due to the decrease in the number of free amine groups in the functionalized albumin as compared to the native albumin.

Albumin Grafting by γ-Irradiation

Albumin was grafted on polypropylene, poly(vinyl chloride), polycarbonate and polyethylene. The surface of a sample to be grafted with albumin was exposed to PBS solution which was previously purged with nitrogen gas. After 30 minutes, PBS was replaced with solution of functionalized albumin solution which was also purged with nitrogen gas. The concentration of the functionalized albumin was varied. The functionalized albumin was allowed to adsorb onto the sample surface for 1 hour under nitrogen. After albumin adsorption, the surface was washed with PBS solution and transferred to nitrogen-purge PBS solution. Then, the albumin-adsorbed sample was exposed to γ-irradiation for various time periods. The γ-irradiated sample was subsequently vacuum dried at room temperature.

The albumin-grafted sample can be stored at room temperature. To make sure that albumin molecules were covalently grafted to the surface, the sample was exposed to 1% sodium dodecylsulfate (SDS) solution at 100° C. for 15 minutes. That treatment removes non-covalently adsorbed albumin molecules from the surface.

Characterization of the Albumin-Grafted Surface

The albumin-grafted surface was characterized by electron spectroscopy for chemical analysis (ESCA), attenuated total reflection-Fourier transform infra-red (ATR-FTIR) spectroscopy and atomic force microscope (AFM), platelet adhesion and activation and albumin retention studies on surface using radiolabeling.

According to ESCA, the surface of albumin-grafted polypropylene fibers included carbon, nitrogen, oxygen, sulfur, sodium, chlorine, and phosphorous, while the control polypropylene fiber surface consisted primarily of carbon and a small amount of oxygen. The albumin grafting on polypropylene fibers was evidenced by the presence of nitrogen and sulfur. Nitrogen values on the albumin-grafted surface ranged from 2.8 to 4.7 atom percent. The observed nitrogen values suggested coating thickness of about 5 nm. This value was calculated with the assumption that albumin was deposited as a thin, uniform film on the polypropylene substrate.

In ATR-FTIR spectroscopy, the polypropylene fibers were placed on a zinc selenide crystal. Samples of control polypropylene, albumin particles, and albumin-grafted polypropylene fibers were examined. The spectrum of the control-grafted polypropylene fibers were examined. The spectrum of the control fiber was digitally subtracted from the spectrum of albumin-grafted fiber. The difference spectrum was similar to the spectrum of albumin particles. This clearly indicated the presence of albumin on the surface.

The comparison of AFM pictures of control fibers and albumin grafted fibers suggested the presence of albumin aggregates on the surface. Since the surface of control fiber itself was not smooth, the image of individual albumin molecules was not obtained. Large aggregates, presumably albumin aggregates, were clearly observed.

Preparation of Samples for Platelet Activation Study

Platelet adhesion and activation on control and albumin grafted samples were examined. The albumin-grafted samples were rehydrated in PBS for at least one hour, if they had been stored in the dried state. The samples were then exposed to heparinized platelet-rich plasma (PRP) at room temperature. The PRP was obtained by centrifuging heparinized human blood at 100 g for five minutes at room temperature.

Platelets were allowed to adhere onto the sample surface for one hour. The samples were then washed with PBS to remove unadherent platelets. The adherent platelets on the samples were fixed with 2% glutaraldehyde in PBS and further stained with Coomassie Brilliant Blue R-250 (CBB) for at least one hour. A solution of 0.1% CBB was made in a mixture of acetic acid, methanol, and water in the ration of 10:45:45. The samples were then observed under video microscope and the total area covered with platelets and thrombi was measured with an image analyzer. The samples were also examined by scanning electron microscopy (SEM).

Effect of Albumin Grafting on Thrombus Formation

The effects of the bulk concentration of functionalized albumin and the γ-irradiation time on the albumin grafting and subsequent inhibition of thrombus formation were examined. The bulk concentration of functionalized albumin for adsorption was varied from 1 mg/ml to 10 mg/ml and the γ-irradiation time was varied from 1 hour to 18 h. The γ-irradiation rate was 0.094 Mrad/h.

FIG. 1 depicts results of the thrombus formation on polypropylene fibers where albumin was grafted under various conditions. The average thrombus-covered surface area ranged from 0 μm² (i.e., no platelet adhesion at all) to more than 2,000 μm² depending on the albumin grafting condition. The data in FIG. 1 shows in general, as the bulk albumin concentration and/or the γ-irradiation time increased, more albumin was grafted and as a result less thrombi were formed on the surface. When the γ-irradiation time increased more than 8 hours, however, the surface became thrombogenic again albeit slightly. It is interesting that the γ-irradiation time beyond 8 hours is not necessarily better in the prevention of thrombus formation.

FIG. 1 suggests that there are more than one optimum conditions for albumin grafting which result in the prevention of thrombus formation. For example, 8 hours of γ-irradiation resulted in almost complete prevention of thrombus formation even when the bulk albumin concentration used for grafting was 1 mg/ml.

At 10 mg/ml of albumin concentration, even one hour of γ-irradiation resulted in dramatic decrease in thrombus formation. Several optimum conditions found in FIG. 1 provide some flexibility in choosing a grafting condition for different applications.

Based on the results of these studies, a concentration of 10 mg/ml of albumin and γ-irradiation time of four hours was chosen for albumin grafting on polyvinyl chloride and polycarbonate. The platelet adhesion and activation on the grafted and control samples were studied by using SEM and image analysis. These studies indicated that grafted samples showed almost no platelets as compared to the ungrafted ones.

Release Of Grafted Albumin upon Exposure to Blood

The functionalized albumin molecules were labeled with $^{125}$I and this radiolabeled albumin was grafted on the polypropylene fibers using the procedure described. Albumin was adsorbed for one hour at the bulk concentration of 10 mg/ml, washed with PBS, and grafted to the surface by γ-irradiation for four hours. These grafted fibers were exposed to whole blood and the surface concentration of the grafted albumin was examined as a function of time after exposure to blood. This study was done to examine the effect of blood on the retention of the grafted albumin. Since the exact surface area of the polypropylene fibers could not be calculated, the radioactivity level was used to examine the stability of the grafted albumin rather than the actual surface albumin concentration.

As a control experiment, radiolabeled albumin was adsorbed on polypropylene fibers at the bulk concentration of 10 mg/ml for one hour. After unabsorbed albumin was washed with PBS, the fibers were kept in PBS for four hours. These fibers containing adsorbed albumin were also exposed to whole blood to study the stability of albumin on the surface.

Figure 2:
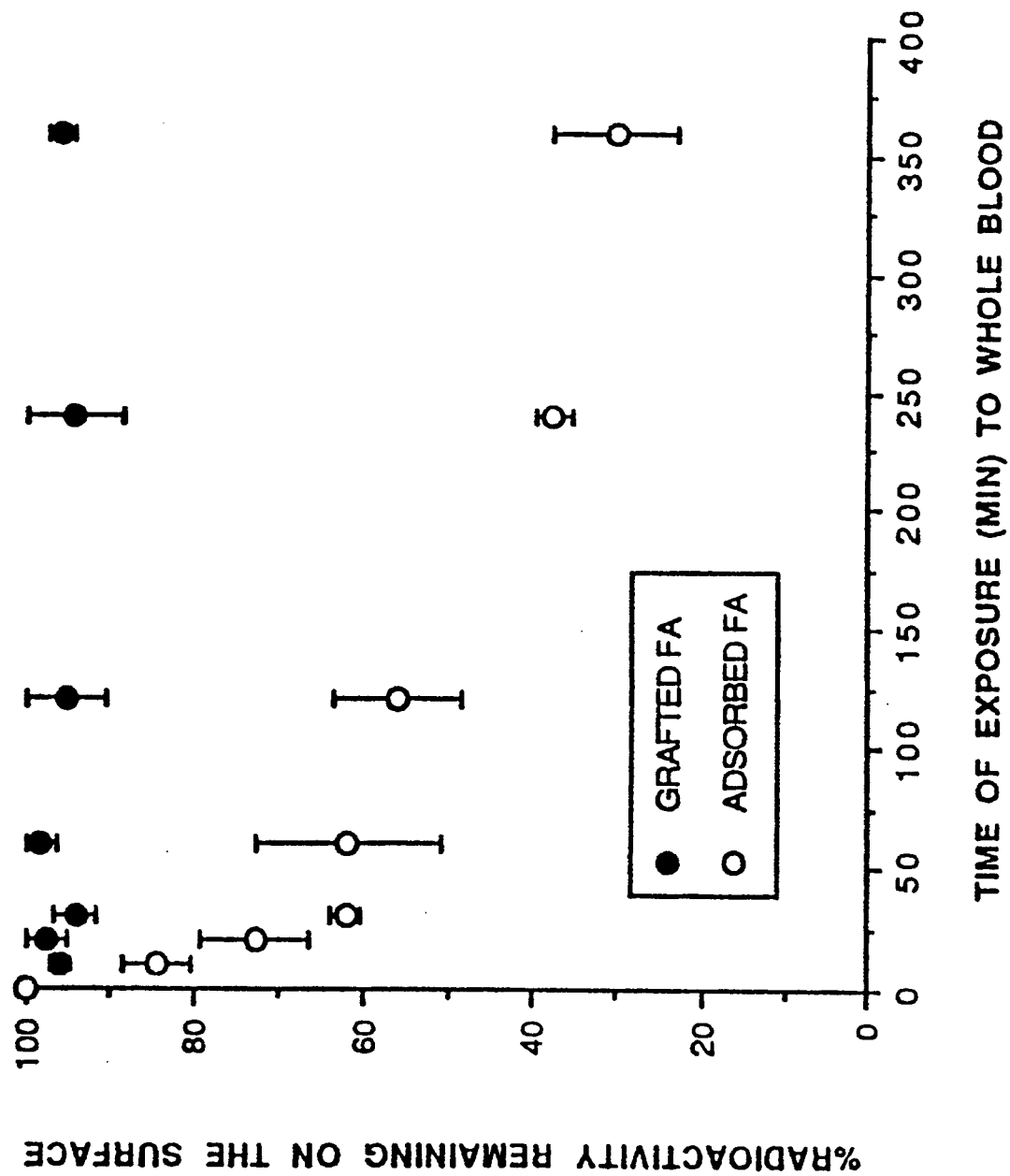
FIG. 2 shows the decrease in the albumin radioactivity after exposure to blood in the static state.

FIG. 2 shows the decrease in the albumin radioactivity after exposure to blood in the static state. The decrease in radioactivity of the grafted albumin was negligible for the first two hours, while that of the ungrafted albumin was reduced by about 50%. Even after six hours of exposure to blood, the radioactivity of the grafted albumin decreased only about 5%; thus, the covalently grafted albumin is stable for up to several hours of blood exposure.

Grafting of Functionalized Albumin On An Adult Hollow Fiber Oxygenator

The oxygenator was first primed with about 500 ml PBS through the venous inlet port. After passing 500 ml more of PBS, the fibers and other components of the oxygenator were allowed to be wetted by PBS for 30 min. by closing the arterial outlet port. The PBS was then replaced by passing 500 ml of desired concentration of functionalized albumin. To ensure that the whole oxygenator received a constant concentration of Functionalized Albumin, an additional 500 ml of Functionalized Albumin was passed after this and allowed to adsorb on the oxygenator components for 1 hour by closing the arterial outlet. After 1 hour, the unabsorbed Functionalized Albumin was washed with 750 ml of PBS. At the end, 500 ml PBS was passed again and retained within the oxygenator, so that irradiation could be carried out in the presence of PBS. The PBS was drained off after irradiating for the desired time interval and the oxygenators were dried in the vacuum chamber at room temperature.

The PVC tubings provided with the oxygenator were treated in the similar manner. Each tubing was first wetted with 7.5 ml PBS for 30 min. The PBS was then replaced by 7.5 ml of desired Functionalized Albumin concentration taking care to avoid introduction of air bubbles. After passing an additional 7.5 ml. of Functionalized Albumin through the tubing it was closed so that Functionalized Albumin could be adsorbed to it for 1 hour. At the end of the adsorption time, the unabsorbed Functionalized Albumin was washed with 25 ml PBS and the tubings were irradiated for required time intervals in the presence of PBS.

Grafting of Functionalized Albumin on Low Density Polyethylene (LDPE)

LDPE was cut into pieces (1 cm × 2.5 cm) and placed in the vials. Functionalized Albumin at 30 mg/ml was adsorbed for 1 hour and unabsorbed Functionalized Albumin was washed with PBS. The adsorbed Functional Albumin was then grafted onto the surface of LDPE by γirradiation. The grafted and control surfaces were subjected to platelet adhesion and activation studies. No platelets could adhere to the surface, if the albumin-adsorbed LDPE was γ-irradiated for 8 hours. As seen with albumin grafting on DDS glass in our previous study, there was an optimum condition for albumin grafting, i.e., 8 hours of γ-irradiation in the presence of PBS.

Once the grafting procedure introduces double bonds to various molecules, the functionalized molecules are grafted to the surface by γ-irradiation. The molecules can be proteins, polysaccharides, synthetic polymers, or phospholipids.

The covalent bonding technique is an improvement over the previous technology discussed in the background herein since albumin can be covalently grafted onto any polymers without premodification of the surface. Grafting may be done on chemically inert polymers such as polypropylene or polyethylene. Since albumin molecules are covalently attached to the surface, no extra caution will be necessary in handling the albumin-grafted polymers for processing such as drying, sterilization, or long-term storage. The albumin on the sample surface can be grafted by a one-step exposure to γ-irradiation. The cost of grafting may be lower than that of other techniques. Most preferably, the grafting can be done on the fully assembled devices which may have complex shape. Thus, the preferred technique allows grafting of albumin to a product such as an adult hollow fiber oxygenator, arterial filter, or PVC tubing and more specifically, the internal surfaces of the fully assembled product which are not readily accessible as for example, an extra corporal blood circuit. This technique can be applied to graff not only albumin but also other proteins (such as gelatin, hemoglobin, tissue plasminogen activator, or hirudin), polysaccharides (such heparin, or dextran), synthetic polymers (such as PEO, or PVP), and various phospholipids.

Grafting by γ-irradiation

Unlike UV light, γ-ray can penetrate polymers quite easily. This is why the surface does not have to be exposed and the grafting can be done on fully assembled devices. Our approach has a great advantage over other techniques in that albumin can be grafted on the fully assembled device. The device can be preexposed to γ-irradiation before adsorbing functionalized albumin.

The adsorbed albumin can be grafted yo the preirradiated surface by increasing the temperature, e.g., to 60° C. Preexposure of the surface to γ-irradiation will result in the formation of peroxides. The peroxides will form radicals upon temperature increase. The formed radicals will result in crosslinking with the functionalized albumin.

Albumin grafting by γ-irradiation can be used regardless of the size, shape and complexity of the device. Grafted albumin is known to improve blood compatibility by preventing the adsorption of platelet-activating proteins such as fibrinogen and the adhesion of platelets. Grafted albumin is effective in inhibiting protein adsorption and platelet activation. Albumin was grafted to the polypropylene porous hollow fibers by gamma irradiation at less than 0.6 Mrad and can be as low as 0.3 Mrad. At those radiation conditions the bulk properties of polypropylene are not effected.

Improved Blood-Compatibility of Oxygenator by Albumin Coating

The platelets were separated from the heparinized pig blood containing acid citrate dextrose by centrifugation. The separated platelets were labeled with indium-111 according to the previously described procedure (Mathias, CI J., and Welch, M. J.: *Seminars in Nuclear Medicine*, 14(2), 118-127, 1984) and then mixed into 2 liters of the hepafinized pig blood. The pig blood containing indium-111 labeled platelets was introduced into the control and albumin-grafted oxygenators.

The control and the albumin-grafted oxygenators were first primed with 450 ml of phosphate buffered saline (PBS) for 1 hour. The PBS in the oxygenators was slowly replaced with the blood containing the radiolabeled platelets. Fractions of the blood coming out of the arterial outlet port of the oxygenators were collected at various time intervals. The effluent blood flow rate was maintained at 6 ml/min. Additional blood was continuously introduced into the oxygenator to compensate for the blood volumes collected. At the end of 1 hour, the blood flow was stopped and all the blood was removed from the oxygenators by washing with 750 ml of PBS.

The oxygenators were then examined with a gamma camera to determine the remaining radioactivity resulting from the adherent platelets. Gamma camera images of the control and albumin-grafted oxygenators in front and side views show higher radioactivity in the control than in the albumin-grafted oxygenator. The count rates ranged from 135-155/sec. for the control while those for the treated were 25-27/sec. The radioactivity on the albumin-grafted oxygenator was less than 20% of that on the control. This verifies that the albumin grafting reduced the platelet adhesion by more than 80%. This test demonstrated that albumin molecules grafted by gamma irradiation are effective in the prevention of surface induced platelet activation.

The ability of the functionalized albumin to form covalent crosslinking with the surface was expected but not obvious because there was no guarantee that the double bonds on albumin will face the surface and form the covalent bonds. The results showed that they did. Albumin grafting occurs only in the presence of water. Since radicals can be generated in the absence of water, the functionalized albumin is expected to be grafted to the surface in the dried state. The functionalized albumin, however, was not grafted to the surface if they were exposed to gamma irradiation in the absence of water. It turned out that the presence of water was necessary to keep albumin molecules in tight contact with the surface by hydrophobic interaction which thereby resulted in covalent grafting.

The ability of the grafted functionalized albumin to prevent surface-induced platelet activation was uncertain. Even if the functionalized albumin was grafted to the surface, it was not obvious whether the grafted albumin was still able to prevent surface-induced platelet activation. Most experts in the biomaterials field thought that the native structure of albumin was critical in the prevention of platelet activation. Based on the steric repulsion theory and experiments it was concluded that the conformation of albumin molecules is not that critical as long as albumin molecules remain flexible. Thus, the ability of the grafted functionalized albumin to prevent surface-induced platelet activation was an unexpected thing to the experts in the field. This ability of the grafted albumin is maintained only if the albumin is grafted under certain conditions as described and finding such conditions was not simple.

The grafted albumin did not block the pores of the porous hollow fibers and the gas transfer is not affected by such grafting.

Grafting albumin as a monolayer on the surface leaves pores intact as evidenced by the gas transfer experiments. No change in the gas transfer has been observed after albumin grafting. The total dosage of gamma ray less than 0.8 Mrad and as low as 0.3 Mrad does not cause changes in the properties of polymers, even polypropylene which is known to be very sensitive to gamma irradiation. The ability to graft albumin with such low dosages is advantageous.

By introducing double bonds to albumin, albumin can be grafted to any polymer substrate with a very low dose of gamma irradiation. The polymer surface does not have to be premodified for grafting. The surface does not have to be exposed, since gamma ray can penetrate polymers quite easily. The use of gamma irradiation allows grafting of albumin to fully assembled devices such as an adult hollow fiber oxygenator. The use of high energy gamma ray for grafting allows grafting of albumin onto any devices regardless of size and shape. Other proteins such as gelatin and hemoglobin and polysaccharide such as dextran have been grafted proving that grafting of diverse molecules including natural and synthetic polymers is possible.

The approach herein can be used even though the surface is not exposed, while photochemical grafting requires surface be exposed. Thermal curing may be used to graff albumin, but it requires long exposure to extremely high temperature, from 100° C. to 160° C. This is not practical. Albumin grafting can be accomplished by irradiation at room temperature even though the surface is not exposed.

What is claimed is:

1. A method of chemically binding a coating to a medical device having a polymeric substrate to make the polymeric substrate compatible for contact with blood including the following steps:

selecting a natural and substantially hydrophilic blood protein for permanent bonding to the polymeric substrate for forming biologically compatible blood contacting surfaces resistant to the formation of thrombin, deposition of formal blood elements or foreign body reaction;

reacting the natural and substantially hydrophilic blood protein with a modifier to functionalize the natural and substantially hydrophilic blood protein to create free radical-reactive sites for bonding the blood protein to the substrate:

applying the functionalized blood protein to coat the polymeric substrate, and creating free radicals on the coated polymeric substrate and the applied functionalized blood protein by irradiating with gamma radiation to initiate a free radical reaction between the substrate and the applied functionalized blood protein.

2. The method of claim 1 wherein the step of reacting the natural and substantially hydrophilic blood protein with a modifier to functionalize the natural and substantially hydrophilic blood protein includes reacting the natural and substantially hydrophilic blood protein with a modifier comprising an epoxy function and an unsaturated double bond.

* * * * *